US012644803B2

(12) United States Patent
Schlaudraff

(10) Patent No.: US 12,644,803 B2
(45) Date of Patent: Jun. 2, 2026

(54) METHOD FOR EXTRACTING A PART OF A MICROSCOPIC SAMPLE

(71) Applicant: LEICA MICROSYSTEMS CMS GMBH, Wetzlar (DE)

(72) Inventor: Falk Schlaudraff, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 621 days.

(21) Appl. No.: 18/178,573

(22) Filed: Mar. 6, 2023

(65) Prior Publication Data

US 2023/0296483 A1 Sep. 21, 2023

(30) Foreign Application Priority Data

Mar. 17, 2022 (EP) ..................................... 22162609

(51) Int. Cl.
*G01N 1/00* (2006.01)
*G01N 1/30* (2006.01)
*G01N 1/31* (2006.01)
*G01N 33/483* (2006.01)

(52) U.S. Cl.
CPC ............... *G01N 1/30* (2013.01); *G01N 1/312* (2013.01); *G01N 33/4833* (2013.01); *G01N 2001/305* (2013.01); *G01N 2001/317* (2013.01)

(58) Field of Classification Search
None
See application file for complete search history.

(56) References Cited

U.S. PATENT DOCUMENTS

| | | | |
|---|---|---|---|
| 6,251,516 B1 | 6/2001 | Bonner et al. | |
| 6,867,038 B2 * | 3/2005 | Liotta .................... G02B 21/32 | |
| | | | 435/363 |
| 10,533,931 B2 | 1/2020 | Schlaudraff et al. | |
| 2006/0023201 A1 | 2/2006 | Malekafzali | |
| 2018/0104948 A1 | 4/2018 | Pierik et al. | |
| 2018/0149561 A1 | 5/2018 | Schlaudraff et al. | |
| 2019/0390252 A1 | 12/2019 | Yeung et al. | |

FOREIGN PATENT DOCUMENTS

| | | |
|---|---|---|
| CA | 2184245 A1 | 9/1995 |
| KR | 20050027610 A | 3/2005 |
| WO | WO 2005/026811 A1 | 3/2005 |

* cited by examiner

*Primary Examiner* — Jyoti Mutreja
(74) *Attorney, Agent, or Firm* — LEYDIG, VOIT & MAYER, LTD.

(57) ABSTRACT

A method includes applying a liquid cover to a microscopic sample to obtain a processed microscopic sample, generating at least one marker for a part of the processed microscopic sample using an imaging system, removing at least a part of the liquid cover from the processed microscopic sample to obtain an uncovered microscopic sample, and extracting a part of the uncovered microscopic sample, based on the at least one marker, to obtain an extracted part.

17 Claims, 4 Drawing Sheets

METHOD FOR EXTRACTING A PART OF A MICROSCOPIC SAMPLE

CROSS REFERENCE TO RELATED APPLICATIONS

This application claims benefit to European Patent Application No. EP22162609.6, filed on Mar. 17, 2022, which is hereby incorporated by reference herein.

FIELD

The present invention relates to a method for extracting a part of a microscopic sample, to a corresponding system and to a computer program.

BACKGROUND

Laser microdissection is a technique for visualizing microscopic samples and cutting part of them out (extracting) using a laser and making such extracted parts available for subsequent molecular biological processes, for example. For this purpose, the samples can be arranged on membrane-based slides, stained gently so as not to damage the biomolecules in the sample to be examined later, visualized and marked for extracting (cutting out). Such laser microdissection with corresponding workflow is described, for example, in U.S. Pat. No. 10,533,931 B2.

Thus, there is a need for improvement in extracting parts of microscopic samples.

SUMMARY

In an embodiment, the present disclosure provides a method comprising applying a liquid cover to a microscopic sample to obtain a processed microscopic sample, generating at least one marker for a part of the processed microscopic sample using an imaging system, removing at least a part of the liquid cover from the processed microscopic sample to obtain an uncovered microscopic sample, and extracting a part of the uncovered microscopic sample, based on the at least one marker, to obtain an extracted part.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
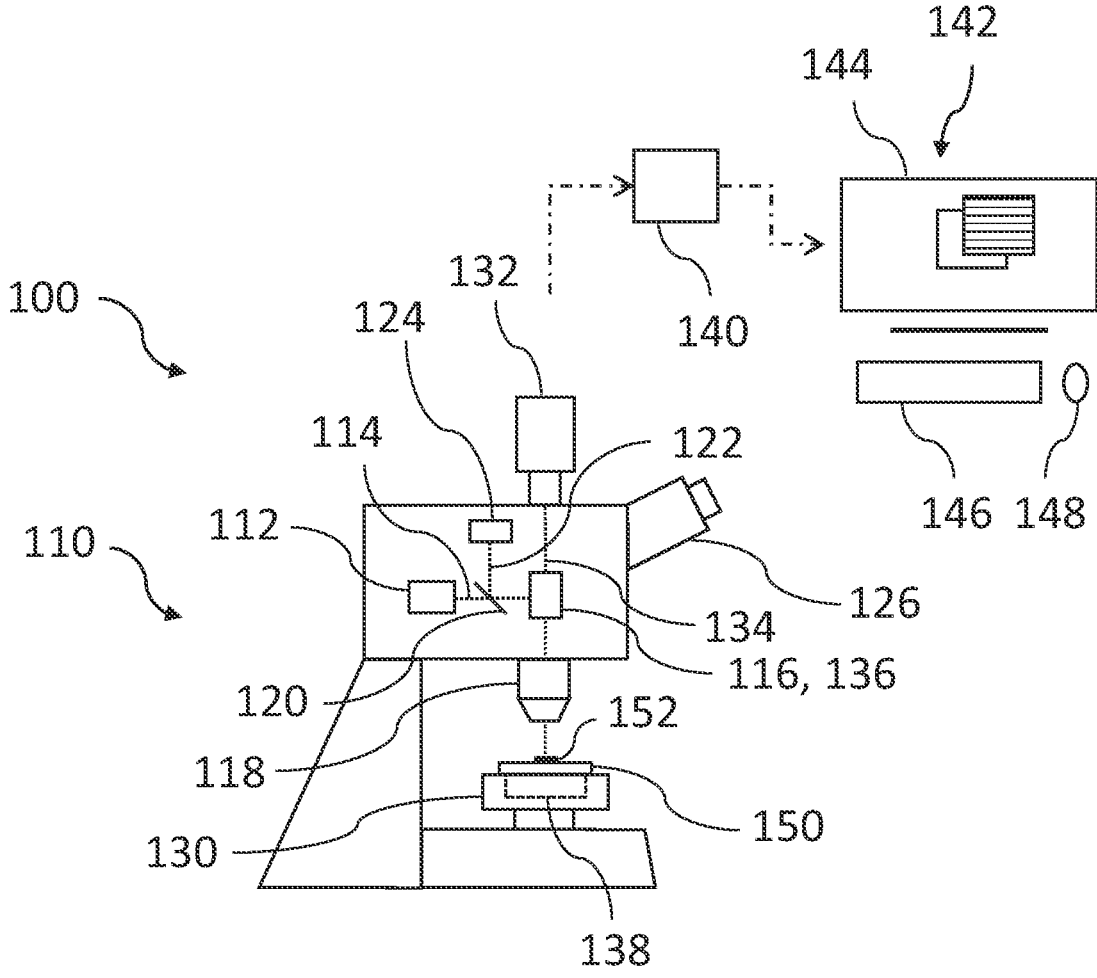
FIG. 1 schematically illustrates a system with an imaging system that can be used for performing a method according to an embodiment of the invention.

An embodiment of the invention relates to a method for extracting a part of a microscopic sample. The method comprises: applying a liquid cover to a microscopic sample to obtain a processed microscopic sample. In an embodiment, said microscopic sample can be treated, e.g., stained, before said liquid cover is applied to said microscopic sample. In an embodiment, said microscopic sample is arranged on a slide. Said slide can be arranged on a stage. Further, at least one marker (or extraction marker) for a part of said processed microscopic sample is generated, using an imaging system like a microscope. Such marker can, preferably, be or comprise one or more individual markers (like points) or also one or more shapes, lines, circles, ellipses, crosses digits etc. Such shapes can, for example, indicate where to cut. Further, at least a part of said liquid cover is removed from the processed microscopic sample to obtain an uncovered microscopic sample. Depending on the specific workflow to be used, the microscopic sample can be removed from the stage and re-arranged there afterwards, for example. Further, a part of the uncovered microscopic sample is extracted, based on the at least one marker, to obtain an extracted part. It is noted that extracting, in particular, refers to physical extracting the part form the microscopic sample; the extracted part can be transferred, e.g. by dropping, catapulting, attachment, into or onto a container, for example.

Applying a liquid cover to a microscopic sample improves generating the markers, in particular due to improving visualisation by means of said imaging system. Applying a liquid cover, in particular, refers to applying a liquid to the surface of the microscopic sample such that the liquid covers the microscopic sample and/or penetrates the microscopic sample. The liquid of the liquid cover, in particular, has a positive effect on light reflected or emitted by the sample. This, accordingly, improves the visualization of the microscopic sample and thus, generating the markers and extracting parts of the microscopic sample.

Such liquid cover (or liquid cover slip) comprises, in an embodiment of the invention, polystyrene and xylene. For example, polystyrene and xylene can be provided in a mixture with both components having the same amount. Such mixture can easily be applied and sufficiently improves the visualization process. Other components, in particular with minor amounts, can be included, for example.

It has been found out, however, that such liquid cover can negatively affect the subsequent processing of the extracted parts. Removing the liquid cover from such extracted parts has turned out to be difficult and time consuming. In particular, for (very) small parts, handling of the parts for removing the liquid cover might even not be possible. The inventors now have recognized that removing the liquid cover, at least in part, from the processed microscopic sample after generating the markers but before extracting the part from the microscopic sample, overcomes such difficulties. Removing such liquid cover from the uncut—and larger—sample is much easier. In an embodiment of the invention, said liquid cover is removed from said processed microscopic sample by means of xylene (as a removing agent). For example, xylene can be applied to the processed microscopic sample for washing the liquid cover away, or the processed microscopic sample can be put into a container filled with xylene.

In an embodiment of the invention, generating said at least one marker for said part of the processed microscopic sample comprises or is based on: visualizing the processed microscopic sample using said imaging system; and determining said at least one marker, based on the visualized processed microscopic sample. This allows monitoring by a user, for example. Also, a user could make inputs for generating the at least one marker in view of the visualized microscopic sample.

According to an embodiment of the invention, said at least one marker is generated digitally and stored for subsequent use for extracting said part of said of the processed microscopic sample. This allows using the imaging system for other tasks while the liquid cover is removed, for example.

According to an embodiment of the invention, said part of the uncovered microscopic sample is extracted by means of laser microdissection. Laser microdissection is a technique allowing fast and precise extraction (cutting out) of even very small parts of microscopic samples.

In an embodiment, a system can be used that comprises said imaging system wherein said system is configured to perform laser microdissection. Such a system can be a microscope system comprising a typical microscope for imaging and, in addition, being configured to perform laser microdissection. Such a combined system allows fast and efficient working. Although such combined system provides specific advantages, it is noted that two different or separate systems can be used—an imaging system like a microscope and a laser microdissection system. This allows, for example, using systems each being specified for the corresponding tasks—imaging (including generating the markers) and laser microdissection.

According to an embodiment of the invention said part of the uncovered microscopic sample is extracted by means of one of the following: cutting the uncovered microscopic sample using needles, applying a buffer solution to the uncovered microscopic sample. Using a template to apply the buffer (or buffer solution) can simplify the process even further. Such techniques are different from laser microdissection but can be used instead of it (or also in addition to it) depending, for example, on the specific needs or the specific microscopic sample. The technique using needles is, preferably, performed automatedly. Similar to the laser microdissection, separate systems might be used for these alternative techniques.

According to an embodiment of the invention said extracted part has a maximum diameter of less than 500 μm. Also, such diameter can be less than 300 μm or less than 100 μm. Alternatively, said extracted part is one of the following: an individual biological cell, a cell cluster of multiple individual cells, an organelle of a biological cell, part of a biological cell, a cell embedding matrix. An organelle or a part of a biological cell can comprise, for example, a nucleus or another specific structure like mitochondria or inclusion bodies of a cell. A cell embedding matrix, in particular, is, for example, extracellular matrix, collagen, connective tissue. It is noted that the size of a cell, organelle or part thereof, can also be less than 500 μm in diameter. In either case, such small parts to be extracted from the microscopic sample are difficult to be handled; thus, the proposed removal of the liquid cover prior to extraction is of particular advantage.

For reliability and verification, pure membrane without sample of the same size can be covered with the same liquid on the same slide and used as negative control for downstream processing subsequently. Thereby possible contaminations by the liquid cover and/or the removing agent, which could alter the results of the downstream analysis, can be detected.

According to an embodiment of the invention, the method further comprises, before said at least part of said liquid cover is removed from the processed microscopic sample: generating at least one reference marker. Such reference marker can be generated at the processed microscopic sample or at said slide, on which the sample is arranged. In case of more than one reference markers, one or more markers can also be generated at each of the sample and the slide. Said method further comprises, after said at least part of said liquid cover is (or has been) removed from the processed microscopic sample: correlating said at least one reference marker with said at least one marker, for extracting said part of the uncovered microscopic sample. In this way, the (extraction) marker can easily and properly be associated with the uncovered microscopic sample, even it was removed from the stage for removing the liquid cover, for example, or if the uncovered microscopic sample is moved, for extraction, to another system that is provided separately from the imaging system.

An embodiment of the invention relates to a system, comprising an imaging system. Said system is configured to: generate at least one marker for a part of a processed microscopic sample, using said imaging system, wherein the processed microscopic sample is a microscopic sample with a liquid cover applied to it. In an embodiment, the system is also configured to (automatically) apply said liquid cover to said microscopic sample. Further, the system is configured to remove at least part of said liquid cover from said processed microscopic sample to obtain an uncovered microscopic sample; and to (physically) extract a part of the uncovered microscopic sample, based on said at least one marker. Such system can be a microscope system with a microscope, for example, and with a device that can transfer the microscopic sample from a stage into a container comprising, for example, xylene, and back to the stage.

According to an embodiment of the invention, the system further is configured to render a user interface, wherein said system is further configured to: visualize the processed microscopic sample on said user interface, using said imaging system; receive input data from said user interface, wherein said input data relates to said at least one marker; and generate said at least one marker for said part of the processed microscopic sample based on said input data.

According to an embodiment of the invention, the system is further configured to perform laser microdissection, wherein said part of the uncovered microscopic sample is extracted by means of laser microdissection. Thus, even liquid covers can be used which would not allow laser cutting as the cover is removed prior to laser application.

With respect to advantages and further embodiments of the system, it is referred to the remarks of the method, which apply here correspondingly.

An embodiment of the invention relates to a computer program with a program code for performing the following steps, when the computer program is run on a processor: correlating at least one reference marker with at least one marker; and controlling a system to extract said part from an uncovered microscopic sample, preferably, by means of laser microdissection. Said at least one marker has been generated for a part of a processed microscopic sample, which is to be removed as mentioned above. The processed microscopic sample is a microscopic sample with a liquid cover applied to it. The uncovered microscopic sample is the processed microscopic sample with the liquid cover removed from it. This allows removing the liquid cover from the microscopic sample after generating the marker(s) but before extracting the part of the microscopic sample.

Further advantages and embodiments of the invention will become apparent from the description and the appended figures.

It should be noted that the previously mentioned features and the features to be further described in the following are usable not only in the respectively indicated combination, but also in further combinations or taken alone, without departing from the scope of the present invention.

FIG. 1 schematically illustrates a system 100 comprising an imaging system 110. In an embodiment, the imaging system 110 can be a microscope and, thus, system 100 can be a microscope system. System 100 can be used for performing a method according to an embodiment of the invention. First, system 100 will be explained in more detail. With respect to FIGS. 2a and 2b, the method will be explained, also with reference to system 100 of FIG. 1.

Imaging system 110 can be used to visualize a microscopic sample 152. In an embodiment, imaging system 110 comprises illumination optics 112 (e.g., comprising a light source) for generating an illumination light beam 114, which is directed, via a reflector 116, to an objective lens 118 and, then, to the microscopic sample 152. Light reflected from the microscopic sample 152 is directed, as an imaging light beam 122, via the objective lens 118, the reflector 116 and a further reflector 120 to a detector 124. Imaging system 110 can in addition, comprise an eyepiece 126 for a user to inspect the microscopic sample.

Note that instead of incident illumination as illustrated in FIG. 1, transmitted light illumination could be used. In the latter case, the illumination light beam would illuminate the sample from below the sample 152.

The imaging system 110 further comprises, in an embodiment, a stage (or microscope stage) 130. The microscopic sample 152 can be arranged on a slide 150, and the slide 150 (with the microscopic sample 152 arranged thereon) can be arranged on the stage 130 such that the microscopic sample 152 can be visualized. In an embodiment, said slide comprises a glass slide with a membrane arranged at or on the glass slide, or a frame slide (e.g., made from metal or plastic) with a membrane arranged in the frame slide. Said microscopic sample 152 is then arranged on said membrane.

In an embodiment, system 100 further comprises a controller or computer 140. System 100 can also comprise a display 144, a keyboard 146 and a computer mouse 148, for example. The system 100 can be configured to render or provide a user interface or graphical user interface 142, illustrated by means of example on the display 144. In this way, images from the microscopic sample 152, acquired by the detector 124, can be received at the controller 140 and displayed via the user interface 142 or the display 144 for a user.

Such system 100 allows visualizing the microscopic sample 152 for a user on the user interface 142, for example. By means of the user interface 142, a user can then also generate input for the system 100 in order to generate markers and/or reference markers for the microscopic sample 152, according to which it may later be extracted.

In an embodiment, system 100 further is configured to perform laser microdissection. In this case, system 100—or, in particular, the imaging system 110 thereof—can comprise a laser 132, which can generate a laser beam 134 that is directed via reflector 116, to objective lens 118 and, then, to the microscopic sample 152. For example, a scanning mirror 136 can be included in reflector 116 or at another appropriate location for directing the laser beam 134 along a desired way around a part of the microscopic sample 152 in order to extract it. Controller 140 might, for example, be used for controlling also laser 132.

In an embodiment, a container 138 is provided, for example, in or at the stage 130. In this way, parts extracted from the microscopic sample and falling downwards. Note that this might require a frame slide with membrane. Depending on the specific kind of laser microdissection arrangement (if laser microdissection is used at all), other kind of containers and/or other locations of containers might be used. The example shown in FIG. 1 is for illustration purposes only.

It is noted that system 100 is an example system that can be used to perform a method according to an embodiment of the invention. Other systems or imaging systems might also be used. In particular, it is not necessary to use a combined system allowing imaging and laser microdissection. A system for laser microdissection that is provided separately from the imaging system can also be used. Also, other extraction methods than laser microdissection might be used.

Figure 2A:
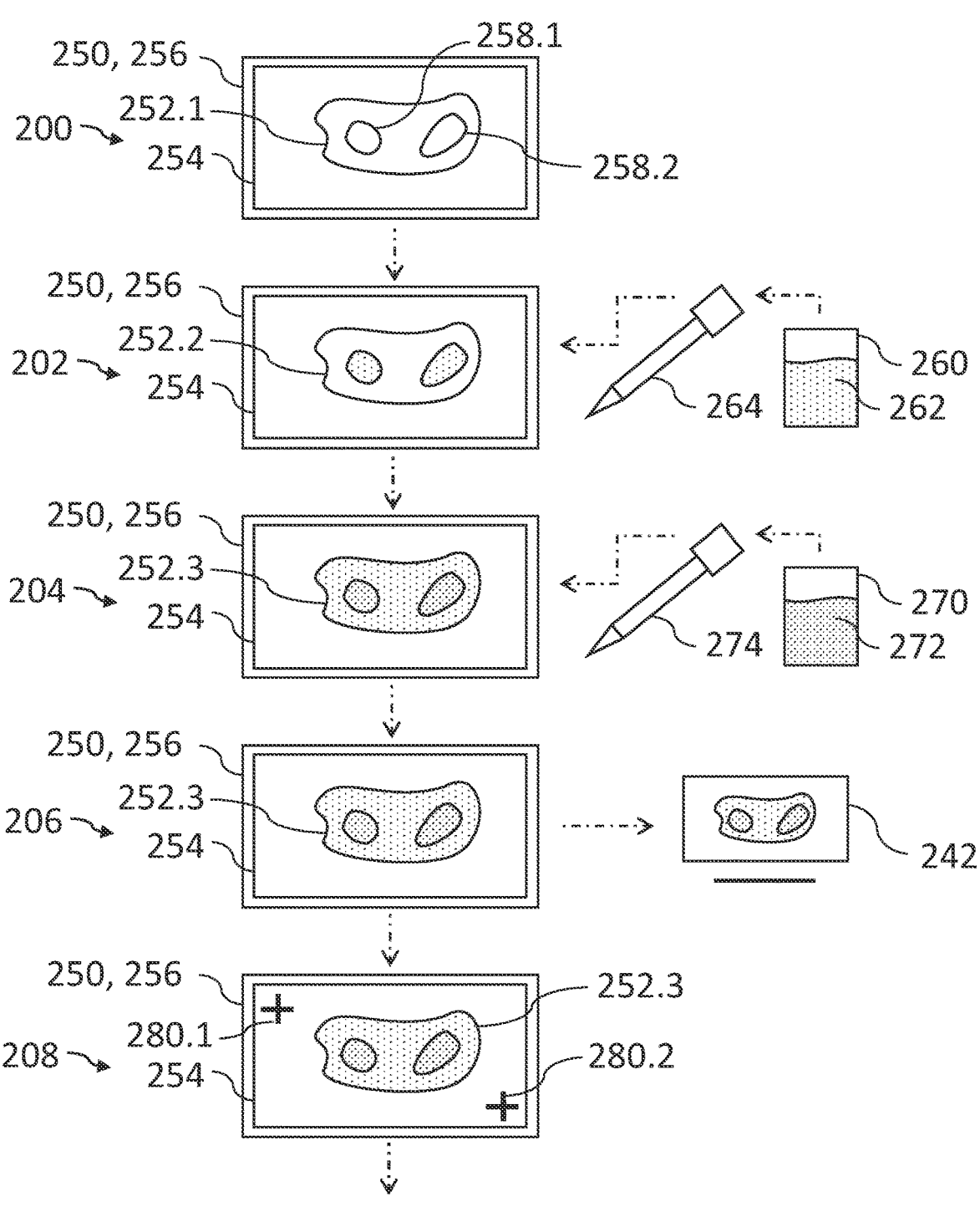
FIGS. 2a and 2b schematically illustrate a method according to an embodiment of the invention.
Figure 2B:
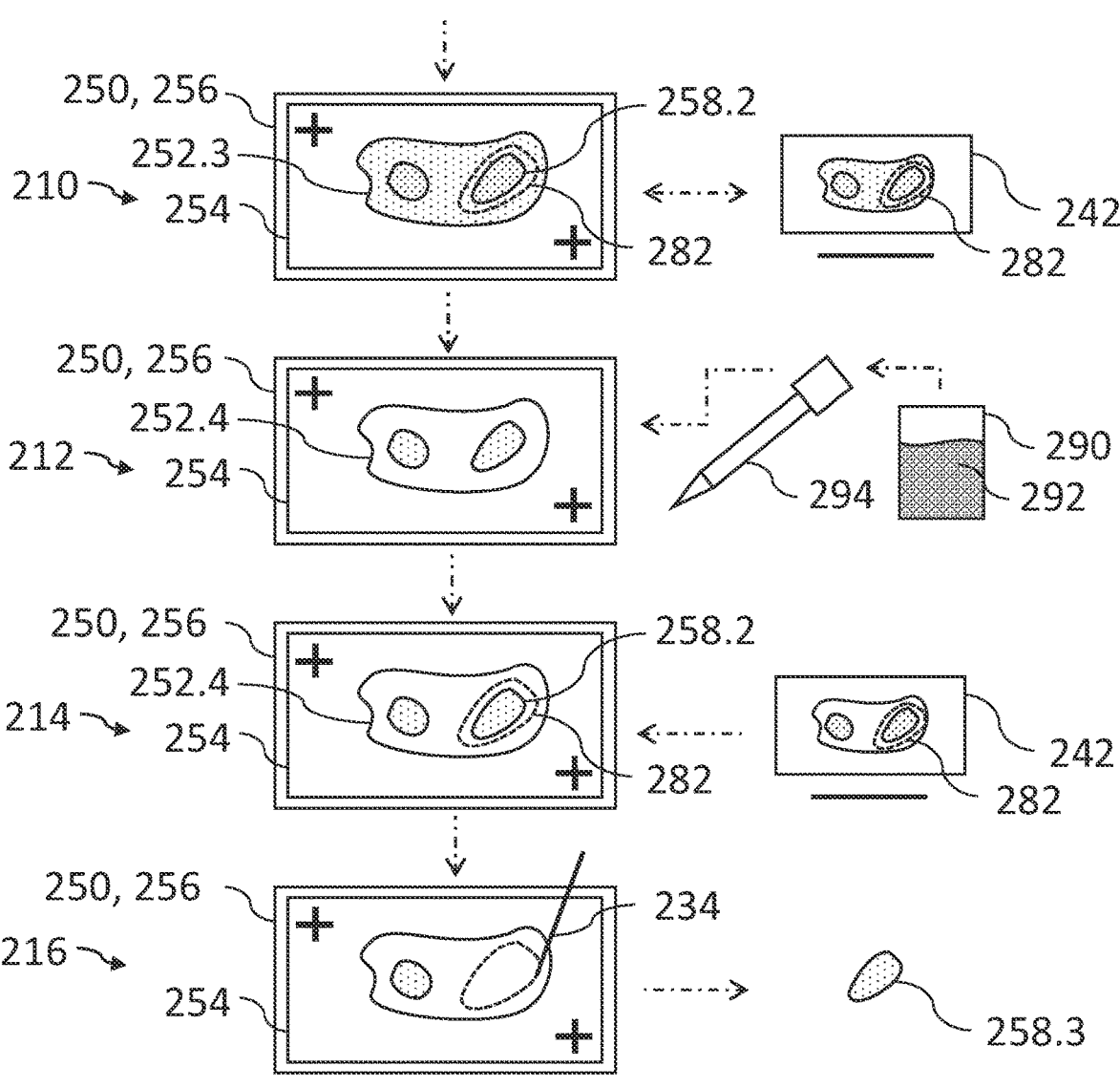

FIGS. 2a and 2b schematically show a method according to an embodiment of the invention by means of a workflow. Note that steps begin in FIG. 2a and continue in FIG. 2b.

In a step 200, a slide 250 is provided. Slide 250 comprises, in an embodiment, a glass or frame slide 256 with a membrane 254 arranged thereon (or therein). Slide 250 can, for example, correspond to slide 150 of FIG. 1. Further, a microscopic sample 252.1 is arranged on the membrane 254. Microscopic sample 252.1 can correspond to microscopic sample 152 of FIG. 1, for example. It is noted that, instead of the glass slide, a frame slide with a membrane arranged therein might be used as mentioned before. Such frame slide might be made of metal like steel or aluminum or the like, for example. Such frame slide might also be made of plastic, for example.

Microscopic sample 252.1 comprises, by means of example, two parts 258.1 and 258.2, which might be of particular interest in the microscopic sample. For example, a user might want one of them or both to be (physically) extracted from the microscopic sample 252.1 for further analysis. These parts 258.1, 258.2 can be, for example, cells or cell organelles like nuclei.

In a step 202, the microscopic sample is treated, for example, stained. This is indicated by means of a container 260 filled with staining material or staining liquid 262. Such staining liquid 262 can be applied, for example by means of a pipette 264, to the microscopic sample. For example, such staining liquid results in a change of color of the parts 258.1, 258.2 but not of the remaining part of the microscopic sample, as illustrated in FIG. 2a for step 202.

After treating or staining, a treated microscopic sample 252.2 is obtained. It is noted that treating may also take place prior to arranging the microscopic sample on the slide or membrane. In addition, it is noted that treating (like staining) may be performed in an automated process and for multiple microscopic samples. A specific treating or staining apparatus might be used. The situation shown in FIG. 2a for step 202 is only for illustration purposes. Further, it is noted that multiple and/or different treating steps may be performed for the same microscopic sample.

In a step 204, a liquid cover is applied to the (treated) microscopic sample in order to obtain a processed microscopic sample 252.3. This is indicated by means of a container 270 filled with liquid cover or liquid 272. Such liquid 272 can be applied, for example by means of a pipette 274, to the microscopic sample in order to cover the microscopic sample with such liquid 272. It is noted that applying the liquid cover may also take place prior to arranging the microscopic sample on the slide or membrane. In this regard it is also noted that step 202 is not a necessary step but is often used in order to indicate specific parts of the microscopic sample by means of staining, for example.

In addition, it is noted that applying the liquid cover may be performed in an automated process and for multiple microscopic samples. A specific application apparatus or device might be used. Such application apparatus or device can, in an embodiment, also be part of integrated into system 100 shown in FIG. 1, for example. The situation shown in FIG. 2a for step 204 is only for illustration purposes.

The liquid cover or liquid 272 (also called liquid cover slip) comprises, in an embodiment, polystyrene and xylene. For example, polystyrene and xylene can be provided in a mixture with both components having the same or almost the same amount (or fraction). Other components, in particular with minor amounts, can also be included. For example, polystyrene can be provided with a fraction between 30% and 70%, and xylene can also be provided with a fraction between 30% and 70%, taking into account that a sum of both fractions has to be equal to or less than 100% (other components may be present). Ideally, the ratio is around 50% to 50%. In another embodiment, the liquid cover or liquid cover material 272 can also comprise water and/or ethanol in a ratio of 25% water and 75% ethanol or higher ethanol amounts up to 100%. Instead of Ethanol, water, polystyrene, xylene, other liquids like acetone, etc. might be used.

In a step 206, the processed microscopic sample 252.3 is visualized. This can be performed by using an imaging system, e.g., a microscope as illustrated in FIG. 1. In particular, the slide 250 with the processed microscopic sample 252.3 can be arranged on a stage like stage 130 shown in FIG. 1. It is noted that slide 250 with the microscopic sample might also be arranged on the stage prior to applying the liquid cover. This might depend on the exact way of how to apply the liquid cover.

Visualizing the processed microscopic sample 252.3 can comprise, for example, acquiring an image (in particular, a real-time or live image) of the processed microscopic sample 252.3 and display or present it at a display of the user interface 242. User interface 242 illustrated in FIG. 2a can correspond to user interface 142 of FIG. 1, for example. In this way, a user can decide where to make or generate markers for extraction, as will be described later.

In a step 208, at least one reference marker is generated. In the example shown in FIG. 2a, two reference markers 280.1 and 280.2 are generated, one on the upper left side of the slide 250 and one on the lower right side of the slide 250. For example, such reference markers can be generated by means the laser of system 100 as shown in FIG. 1 in that the membrane 254 of the slide 250 is cut at the positions where the reference markers 280.1 and 280.2 are shown. Such reference marker(s) can be used for better or more precisely associating the (extraction) marker with the microscopic sample (what will be described later). This is of particular interest in case that re-arranging the slide 250 at the stage is necessary, if the slide 250 has to be removed from the stage for one of the following steps.

It is noted that associating the (extraction) marker with the microscopic sample is, in general, also possible without such reference marker(s). Thus, step 208 is an optional step. It is also noted that step 208 can take place prior to step 206.

In step 210, at least one marker or extraction marker 282 is generated. In an embodiment, this is based on the visualized processed microscopic sample 252.3 as shown in FIG. 2b for step 210 on the right side. Thus, step 206, in which the processed microscopic sample 252.3 is visualized can be considered as a part or sub-step of step 210.

In the example shown, part 258.2 of the microscopic sample is to be extracted. Thus, a marker 282 is generated that encircles the part 258.2 with, for example, a certain distance. In the shown example, marker 282 is a line. However, other types of marker are possible, for example, multiple points and/or several sections of lines or other shapes or the like. If multiple parts are to be extracted, multiple lines as markers can also be generated. Such marker(s), in particular, shall indicate where a laser beam (in case of laser microdissection) has to be guided around the part to be extracted. Such marker(s) shall, in particular, be generated such that a width of the laser beam is considered for a distance of the marker(s) from the part to be extracted. This is, the laser shall not hit the part to be cut out but shall cut the membrane only next to the part.

Generating such markers can be performed using the user interface 242. For example, a user can view the visualized processed microscopic sample 252.3 on the user interface 242 or the display thereof and draw a line (as the marker) using the user interface 242 or the computer mouse thereof. It is noted that generating such markers does not necessarily need any input from the user; such process can also be performed automatedly, for example, by means of image analysis finding contours of the stained parts.

In either case, the liquid cover applied to the microscopic sample improves the image of the microscopic sample, which a user can view or an image analysis process can use. A reason for this improved visibility is, for example, that the liquid applied to the microscopic sample affects light emission and/or reflection by the sample in a positive way.

In an embodiment, relative coordinates between the reference markers(s) and the (extraction) marker(s) can also be determined in step 210. These relative coordinates can later be used to correlate the reference markers(s) and the (extraction) marker(s).

It is noted that the marker 282 in practice will, typically, not be visible at the microscopic sample or slide itself but only on the user interface. The marker 282 shown on the left side of step 210 in FIG. 2b is for illustration purposes only. Rather, the marker or extraction marker 282 can be generated digitally. Once the marker 282 has been generated, it can be stored for subsequent use for extracting said part of the processed microscopic sample. For example, the marker can be stored in the controller or computer 140 shown in FIG. 1 or a storing device thereof.

In a step 212, the liquid cover is removed from the processed microscopic sample in order to obtain an uncovered microscopic sample 252.4. Such liquid cover can be removed by, for example, applying another liquid (removing agent) to the processed microscopic sample. This is indicated by means of a container 290 filled with liquid or removing liquid 292. Such liquid 292 can be applied, for example by means of a pipette 294, to the microscopic sample. Another preferred way is to immerse the processed microscopic sample into such liquid. For example, processed microscopic sample might be immersed into the liquid 292 in container 290. This step can comprise removing the slide 250 with the processed microscopic sample 252.3 arranged thereon from the stage.

In an embodiment, said liquid 292 is or comprises xylene. By immersing the processed microscopic sample into the xylene for a certain amount of time, for example 20 or 30 seconds, the liquid cover can be removed from the microscopic sample. Additional steps might be performed in order to remove any remaining xylene from the microscopic sample. To achieve that, warming or heating of the sample could be applied to vaporize the xylene quickly; at room temperature it will vaporize as well. Using desiccant like silica gel to dry the sample is a suitable approach as well. Typically, however, remaining xylene will not negatively affect further examination of nucleic acids by PCR-based methods of the microscopic sample or extracted parts thereof.

In addition, it is noted that removing the liquid cover may be performed in an automated process and/or for multiple microscopic samples. A specific removal apparatus or device might be used. Such removal apparatus or device can, in an embodiment, also be part of or integrated into system 100 shown in FIG. 1, for example. The situation shown with step 212 is only for illustration purposes.

In step 214, the slide 250 with the uncovered microscopic sample can be re-arranged at the stage. The previously stored marker 282 can be loaded (into a program running on a processor or the controller 140 of FIG. 1, for example) and, for example, also be shown via the user interface 242. The reference markers 280.1, 280.2 can be used and correlated with the marker 282; this can be based, for example, on the relative coordinates having been determined in step 210.

Such reference markers 280.1, 280.2, in particular, can be used to place the marker 282 at the correct position with respect to the part 258.2, just as it has been previously defined. In this regard it is noted that the position of the reference marker(s) relative to the microscopic sample and its parts to be extracted, did not change.

Correlating the reference marker(s) and the (extraction) marker(s) can, for example, be performed within a program running on a processor or the controller 140 of FIG. 1, for example, as mentioned before.

It is noted that step 214 can be omitted in case the slide 250 with the microscopic sample did have to be removed from the stage for removing the liquid cover. In addition, it is noted that the slide 250 with the uncovered microscopic sample 252.4 can also be arranged at another stage of another system, in case separate systems are used for generating the markers and for extracting the part, as mentioned above. In such case, the previously stored marker 282 can be transferred to such other system for extraction. Also, the relative coordinates between the reference markers(s) and the (extraction) marker(s) can also be stored after having been determined (in step 210), and then also be transferred.

In step 216, part 258.2 of the uncovered microscopic sample 252.4 is (physically) extracted from the uncovered microscopic sample 252.4. This is performed based on the marker 282. In this way, an extracted part 258.3 is obtained, which can be further examined or processed. In the embodiment shown in FIG. 2b, extraction is being performed by means of laser microdissection. In such case, laser beam 234 (which can correspond to laser beam 134 of FIG. 1) can be controlled to follow the marker 282 (it can be a line) and, thus, cutting the part 258.2 out from the microscopic sample.

Depending on the specific kind of the system used for laser microdissection, the dissected or extracted part 252.3 can, for example, be dropped into a collecting container (as mentioned for FIG. 1) or be transported into a container in other ways.

As mentioned before, slide 250 can comprise, for example, a glass slide with a membrane arranged thereon. For such glass slides, the membrane can settle on the glass and then stick to the glass. For example, liquid (for example, from the liquid cover or the liquid used to remove the liquid cover) can get between the membrane and the glass through a hole in the membrane and the membrane can be attached to the glass by capillary forces. This holds true in particular for non-contact laser microdissection (LMD) systems. Such holes might arise from generating the mentioned reference markers.

Such sticking of the membrane might result in extracted parts not falling off the slide or not being able to be catapulted away, for example. This can easily be overcome, for example, by providing one or more defocused laser pulses into the middle of small dissectate areas (i.e., parts having been cut out; e.g., with diameter of 1-40 μm). To the contrary, this can contribute to the membrane no longer being able to shift relative to the reference markers. Corresponding defocused laser pulses can be centered to simplify the collection.

Figure 3:
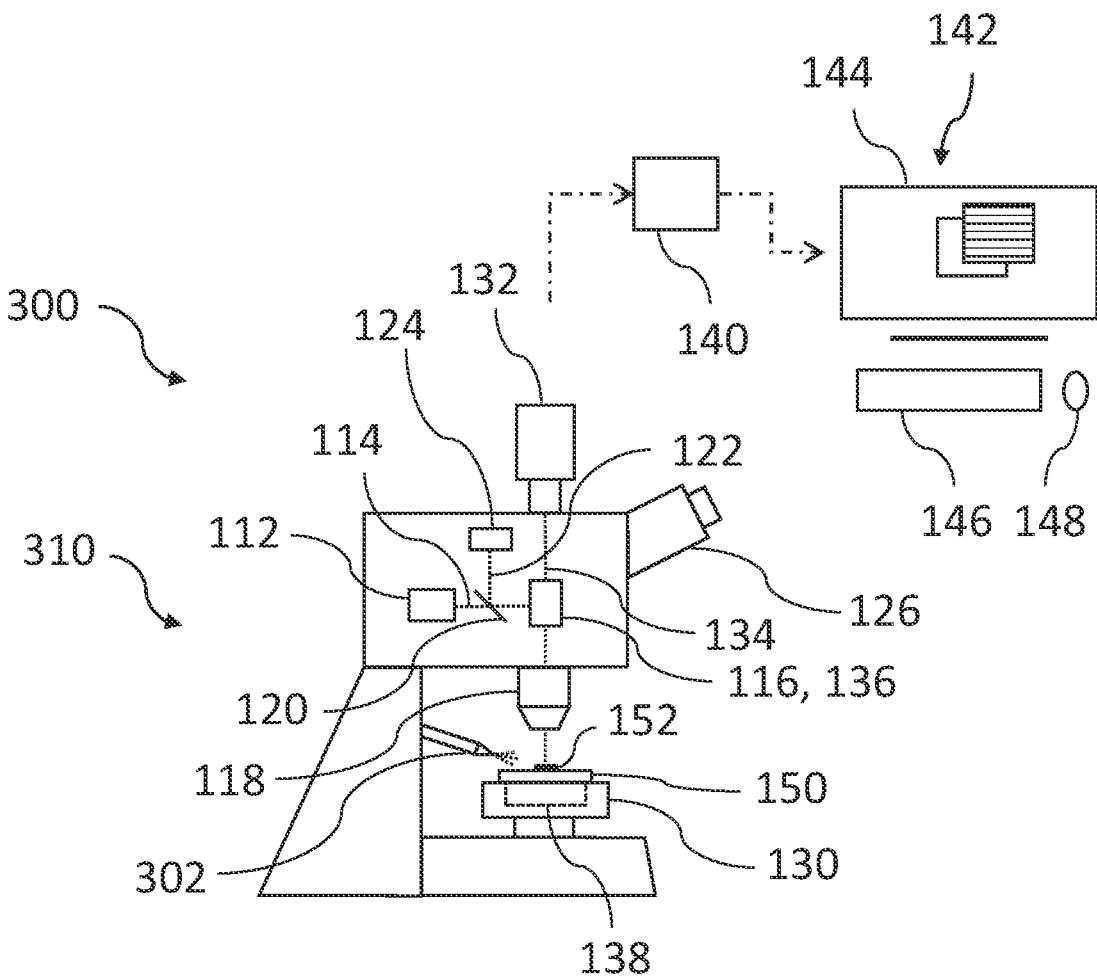
FIG. 3 schematically illustrates another system with an imaging system that can be used for performing a method according to an embodiment of the invention.

FIG. 3 schematically illustrates a system 300 comprising an imaging system 310. System 300 corresponds to system 100 of FIG. 1, and imaging system 310 corresponds to imaging system 110 of FIG. 1. The same reference numerals as in FIG. 1 are, thus, used. For explanation it is referred to FIG. 1

A difference between system 300 and system 100 is that a pipe 302 is provided, which is configured to apply liquid to the microscopic sample 152, for example by spraying. In particular, such liquid can be the liquid for the liquid cover (e.g., liquid 272 of FIG. 2a). In addition, or alternatively, such liquid can be the liquid for removing the liquid cover (e.g., liquid 292 of FIG. 2b). Also, another (additional) pipe might be used for the removing liquid. Controller 140 can be configured to control such pipe 302 in order to apply such liquid to the microscopic sample 152. In this way, the system 300 is configured to apply the liquid cover to the microscopic sample and/or to remove the liquid cover from the microscopic sample.

It is noted that system 300 is only for illustration purposes; other configurations of a system configured to apply and/or remove the liquid cover can be used. For example, such system can comprise a robot configured to remove the slide from the stage, immerse it into liquid, and re-arrange the slide at the stage.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to a microscope comprising a system as described in connection with one or more of the FIGS. 1 to 3. Alternatively, a microscope may be part of or connected to a system as described in connection with one or more of the FIGS. 1 to 4. FIG. 3 shows a schematic illustration of a system 300 configured to perform a method described herein. The system 3 comprises an imaging system or microscope 310 and a computer system or controller 140. The imaging system or microscope 310 is configured to take images and is connected to the computer system 140. The computer system 140 is configured to execute at least a part of a method described herein. The computer system 140 may be configured to execute a machine learning algorithm. The computer system 140 and imaging system or microscope 310 may be separate entities but can also be integrated together in one common housing. The computer system 140 may be part of a central processing system of the imaging system or microscope 310 and/or the computer system 140 may be part of a subcomponent of the imaging system or microscope 310, such as a sensor, an actor, a camera or an illumination unit, etc. of the imaging system or microscope 310.

The computer system 140 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 140 may comprise any circuit or combination of circuits. In one embodiment, the computer system 140 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 140 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 140 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 140 may also include a display device, one or more speakers, and a keyboard and/or controller, which can include a mouse, trackball, touch screen, voice-recognition device, or any other device that permits a system user to input information into and receive information from the computer system 140.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

An embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. An embodiment of the present invention is an apparatus as described herein comprising a processor and the storage medium.

An embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

An embodiment comprises a computer having installed thereon the computer program for performing one of the methods described herein.

An embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

100, 300 system
1010, 310 imaging system
112 illumination optics
114 illumination light beam
116 reflector
118 objective lens
120 reflector
122 imaging light beam
124 detector
126 eyepiece
130 stage
132 laser
134, 234 laser beam
136 scanning mirror
138 container
140 controller
142, 242 user interface
144 display
146 keyboard
148 computer mouse
150, 250 slide
152, 252.1 microscopic sample
200-216 method steps
252.2 treated microscopic sample
252.3 processed microscopic sample
252.4 uncovered microscopic sample
254 membrane
256 glass slide
258.1, 258.2 part of the microscopic sample
258.3 extracted part
260 container
262 staining liquid
264 pipette
270 container
272 liquid cover
274 pipette
280.1, 280.2 reference marker
282 marker
269 container
292 removing liquid
294 pipette
302 pipe

The invention claimed is:

1. A method for extracting a part of a microscope sample comprising:
   applying a liquid cover to a microscopic sample to obtain a processed microscopic sample, wherein the liquid cover is configured to improve visualization of the microscopic sample;
   generating at least one marker for a part of the processed microscopic sample using an imaging system;
   after generating the at least one marker, removing, using a liquid removing agent, at least a part of the liquid cover from the processed microscopic sample to obtain an uncovered microscopic sample; and
   after removing the at least part of the liquid cover, extracting a part of the uncovered microscopic sample, based on the at least one marker, to obtain an extracted part.

2. The method of claim 1, wherein generating the at least one marker for the part of the processed microscopic sample comprises or is based on:
   visualizing the processed microscopic sample using the imaging system; and
   determining the at least one marker, based on the visualized processed microscopic sample.

3. The method of claim 1, wherein the at least one marker is generated digitally and stored for subsequent use for extracting the part of the uncovered microscopic sample.

4. The method of claim 1, wherein the part of the uncovered microscopic sample is extracted by laser microdissection.

5. The method of claim 4, wherein a system comprising the imaging system is configured to perform laser microdissection, and wherein the part of the uncovered microscopic sample is extracted by laser microdissection.

6. The method of claim 1, wherein the part of the uncovered microscopic sample is extracted by one of the following: cutting the uncovered microscopic sample using needles, and applying a buffer solution to the uncovered microscopic sample.

7. The method of claim 1, wherein the liquid cover comprises polystyrene and xylene.

8. The method of claim 7, wherein the at least part of the liquid cover is removed from the processed microscopic sample by xylene.

9. The method of claim 1, wherein the extracted part has a maximum diameter of less than 500 μm or wherein the extracted part is one of the following: an individual biological cell, a cell cluster of multiple individual cells, an organelle of a biological cell, part of a biological cell, and a cell embedding matrix.

10. The method of claim 1, wherein the microscopic sample is arranged on a slide,
   wherein the slide comprises a glass slide with a membrane arranged on the glass slide, or a frame slide with a membrane arranged in the frame slide, and
   wherein the microscopic sample is arranged on the membrane.

11. The method of claim 1, wherein the microscopic sample is treated before the liquid cover is applied to the microscopic sample to obtain the processed microscopic sample.

12. The method of claim 1, further comprising:
   before the at least part of the liquid cover is removed from the processed microscopic sample, generating at least one reference marker; and
   after the at least part of the liquid cover is removed from the processed microscopic sample, correlating the at least one reference marker with the at least one marker, for extracting the part of the uncovered microscopic sample.

13. A system for extracting a part of a microscope sample, the system comprising:
   an imaging system configured to:
      generate at least one marker for a part of a processed microscopic sample, wherein the processed microscopic sample is a microscopic sample with a liquid cover applied to it, and wherein the liquid cover is configured to improve visualization of the microscopic sample;

remove, after generating the at least one marker, at least a part of the liquid cover from the processed microscopic sample using a liquid removing agent to obtain an uncovered microscopic sample; and extract, after removing the at least part of the liquid cover, the part of the uncovered microscopic sample based on the at least one marker.

14. The system of claim 13, further configured to:

render a user interface;

visualize the processed microscopic sample on the user interface, using the imaging system;

receive input data from the user interface, wherein the input data relates to the at least one marker; and generate the at least one marker for the part of the processed microscopic sample, based on the input data.

15. The system of claim 13, further configured to apply the liquid cover to the microscopic sample.

16. The system of claim 13, further configured to perform laser microdissection, wherein the part of the uncovered microscopic sample is extracted by laser microdissection.

17. A non-transitory computer-readable medium having processor-executable instructions stored thereon, wherein the processor-executable instructions, when executed by one or more processors, facilitate performance of a method comprising:

correlating at least one reference marker with at least one marker, wherein the at least one marker has been generated for a part of a processed microscopic sample, wherein the processed microscopic sample is a microscopic sample with a liquid cover applied to it, wherein the liquid cover is configured to improve visualization of the microscopic sample; and controlling a system to extract the part from an uncovered microscopic sample, wherein the uncovered microscopic sample is the processed microscopic sample with the liquid cover removed from it, wherein at least a part of the liquid cover is removed from the processed microscopic sample using a liquid removing agent after the at least one marker has been generated, and wherein extracting the part from the uncovered microscopic sample is after removing the at least part of the liquid cover.

\* \* \* \* \*